United States Patent
Avallin et al.

(10) Patent No.: US 11,291,929 B2
(45) Date of Patent: Apr. 5, 2022

(54) METHOD AND SYSTEM FOR TRANSFERRING SEPARATION RESIN

(71) Applicant: Cytiva Sweden AB, Uppsala (SE)

(72) Inventors: Johan Avallin, Uppsala (SE); Klaus Gebauer, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 0 days.

(21) Appl. No.: 16/481,655

(22) PCT Filed: Jan. 30, 2018

(86) PCT No.: PCT/EP2018/052187
§ 371 (c)(1),
(2) Date: Jul. 29, 2019

(87) PCT Pub. No.: WO2018/141701
PCT Pub. Date: Aug. 9, 2018

(65) Prior Publication Data
US 2020/0001204 A1    Jan. 2, 2020

(30) Foreign Application Priority Data
Jan. 31, 2017 (GB) ..................... 1701576

(51) Int. Cl.
*B01D 15/20* (2006.01)
*G01N 30/56* (2006.01)
*A61L 2/08* (2006.01)

(52) U.S. Cl.
CPC ............ *B01D 15/206* (2013.01); *A61L 2/081* (2013.01); *G01N 30/56* (2013.01); *G01N 2030/565* (2013.01)

(58) Field of Classification Search
CPC ....... B01D 15/206; A61L 2/081; G01N 30/56; G01N 2030/565; B65B 3/04
(Continued)

(56) References Cited

U.S. PATENT DOCUMENTS 626,950 A    6/1899 Wheelwright
2,006,393 A    7/1935 Hapgood
(Continued)

FOREIGN PATENT DOCUMENTS

CN    2021155132 U    3/2012
CN    204841030 U    12/2015
(Continued)

OTHER PUBLICATIONS

PCT International Search Report and Written Opinion for PCT Application No. PCT/EP2018/052187 dated May 15, 2018 (11 pages).
(Continued)

*Primary Examiner* — Timothy P. Kelly
*Assistant Examiner* — Stephanie A Shrieves
(74) *Attorney, Agent, or Firm* — Eversheds Sutherland (US) LLP

(57) ABSTRACT

A method and a system and a container system for transferring separation resin from at least one first container (3; 3; 3a, 3b; 3a', 3b', 3c', 3d) to a second container (5; 5'), wherein said first container is a deformable, single-use separation resin storage container, said method comprising the steps of:—preparing (S1) the at least one first container by providing a deformable, single-use container comprising an outlet port (4') with a predefined volume of separation resin in a storage solution;—fluidizing (S3) the separation resin in the at least one first container to provide a resin slurry, said fluidizing being performed by mechanical interaction to the first container from an outside of the first container to provide a deformation of said first container;—fluidically connecting (S5) the outlet port (4') of the at least one first container to an inlet port (103) of the second container;—transferring (S7) separation resin from the at least one first container to the second container by generat-
(Continued)

ing a pressure difference between an interior of the second container and an interior of the first container where the pressure is lower in the second container.

14 Claims, 10 Drawing Sheets

(58) Field of Classification Search
USPC .......................................................... 141/10
See application file for complete search history.

(56) References Cited

U.S. PATENT DOCUMENTS

| | | | |
|---|---|---|---|
| 2,075,678 A | | 3/1937 | Langen |
| 2,982,247 A | | 5/1961 | Varest et al. |
| 2,999,500 A | * | 9/1961 | Schurer ................ A61M 1/0011 604/322 |
| 3,078,847 A | | 2/1963 | Wandell et al. |
| 3,098,819 A | | 7/1963 | Sager |
| 3,675,670 A | | 7/1972 | Ogawa |
| 3,863,664 A | | 2/1975 | Holbrook et al. |
| 4,045,004 A | | 8/1977 | Berger |
| 4,195,672 A | * | 4/1980 | Freeman ............... A01M 7/0092 141/231 |
| 4,250,035 A | | 2/1981 | McDonald et al. |
| 4,263,144 A | | 4/1981 | Platt |
| 4,388,922 A | * | 6/1983 | Telang ................... A61M 1/005 141/35 |
| 4,467,915 A | * | 8/1984 | Snyder ................... B65D 77/06 206/219 |
| 5,213,683 A | | 5/1993 | Mann |
| 5,282,973 A | * | 2/1994 | Mann ................... B01D 15/206 210/198.2 |
| 5,423,982 A | | 6/1995 | Jungbauer et al. |
| 5,875,925 A | | 3/1999 | Stevens |
| 5,876,511 A | | 3/1999 | Till |
| 6,065,860 A | | 5/2000 | Fuchsbichler |
| 6,402,958 B1 | * | 6/2002 | Moran ................. B01D 15/206 141/12 |
| 6,446,679 B2 | * | 9/2002 | Hofmann ............... G01N 30/56 141/1 |
| 6,463,952 B1 | | 10/2002 | Stevens |
| 6,684,500 B1 | | 2/2004 | Kohlhase et al. |
| 6,740,241 B1 | * | 5/2004 | Dickson ................ B01D 15/08 141/12 |
| 7,770,762 B2 | | 8/2010 | Arghyris et al. |
| 8,133,395 B2 | | 3/2012 | Karlsson et al. |
| 10,940,402 B2 | * | 3/2021 | Avallin ................ B01D 15/206 |
| 2002/0153221 A1 | | 10/2002 | Schnepf |
| 2003/0183299 A1 | | 10/2003 | Talamona |
| 2005/0242018 A1 | | 11/2005 | Hodgin et al. |
| 2007/0090053 A1 | * | 4/2007 | Windahl ............. G01N 30/6021 210/656 |
| 2007/0215548 A1 | * | 9/2007 | Zhou ...................... B01J 20/267 210/656 |
| 2008/0217248 A1 | * | 9/2008 | Gebauer .............. B01D 15/206 210/656 |
| 2009/0007643 A1 | | 1/2009 | Svensson et al. |
| 2009/0188211 A1 | * | 7/2009 | Galliher .............. B01F 15/0085 53/434 |
| 2010/0046322 A1 | | 2/2010 | Nordberg et al. |
| 2011/0053127 A1 | * | 3/2011 | Karlberg .............. B01D 15/206 434/219 |
| 2011/0100932 A1 | | 5/2011 | Lonnqvist et al. |
| 2011/0126936 A1 | * | 6/2011 | Dawson ................ B65B 31/024 141/10 |
| 2011/0259831 A1 | * | 10/2011 | Brandt ................... G01N 30/56 210/741 |
| 2012/0168205 A1 | | 7/2012 | Hwang et al. |
| 2012/0255642 A1 | * | 10/2012 | Gebauer .............. B01D 15/206 138/118.1 |
| 2013/0062267 A1 | * | 3/2013 | Gebauer ............... B01D 15/14 210/198.2 |
| 2013/0186834 A1 | * | 7/2013 | Vicalvi ............... B01F 7/00141 210/656 |
| 2013/0228501 A1 | * | 9/2013 | Lefebvre ................ F16L 33/00 210/198.2 |
| 2015/0368602 A1 | * | 12/2015 | Galliher ................ C12M 47/10 210/767 |
| 2016/0228790 A1 | * | 8/2016 | Bjorling .............. B01D 15/206 |
| 2016/0324995 A1 | | 11/2016 | Delaunay et al. |
| 2019/0151569 A1 | | 5/2019 | Fangrow et al. |

FOREIGN PATENT DOCUMENTS

| | | | |
|---|---|---|---|
| EP | 1566631 A | * | 8/2005 |
| EP | 1566631 A1 | | 8/2005 |
| JP | 08136522 H | | 5/1995 |
| JP | 2000205900 | | 7/2000 |
| JP | 2004004093 A | | 1/2003 |
| JP | 2012159462 A | | 8/2012 |
| WO | WO-1990011963 A1 | * | 10/1990 |
| WO | 2007/067882 A2 | | 6/2007 |
| WO | 2009/032903 A1 | | 3/2009 |
| WO | 2009/093953 A1 | | 7/2009 |
| WO | 2011/076386 A1 | | 6/2011 |
| WO | 2012/040574 A1 | | 3/2012 |
| WO | 2015/047172 A1 | | 4/2015 |

OTHER PUBLICATIONS

GB Search Report for GB Application No. 1701576.9 dated Aug. 29, 2017 (3 pages).
Chinese Office Action for CN Application No. 201880009331.8 dated Jan. 14, 2021 (21 pages, with English translation).
CN CPME1941258P.2021020, Application No. 201780073867.1 First Office Action with English Translation, dated Feb. 2, 2021 (58 pages).
CN CPME1941258P.2021020, Application No. 201780073867.1 Second Office Action with English Translation, dated Sep. 23, 2021 (23 pages).
FER Government of India Examination Report Under Sections 12 & 13 of the Patents Act, 1970 and the Patents Rules, 2003, Application No. 201917010790, dated Nov. 27, 2020 (6 pages).
JP 313924-JP-5 Office Action with English Translation, dated Jul. 5, 2021 (9 pages).
PCT Search Report dated Dec. 15, 2017 (13 pages).

* cited by examiner

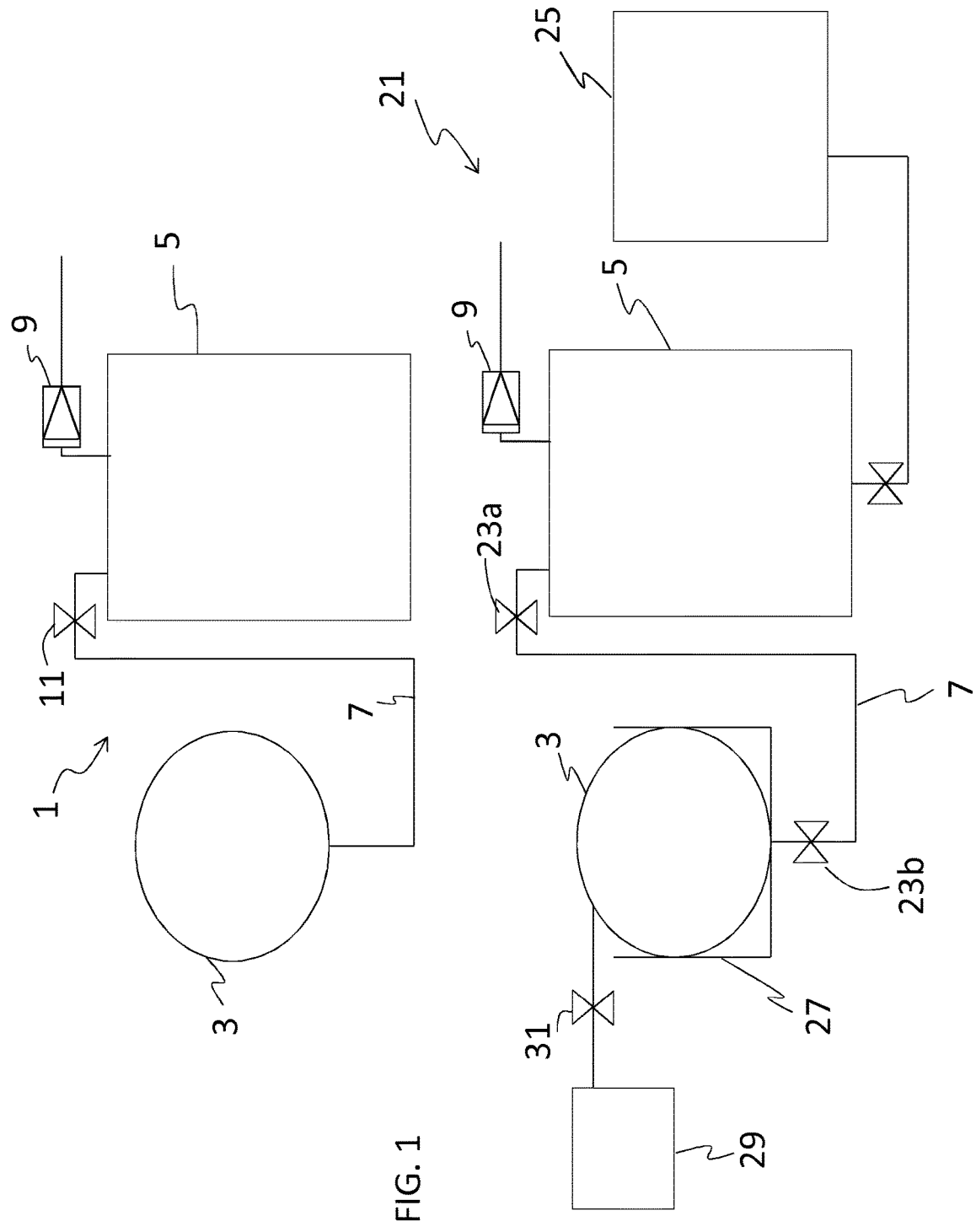

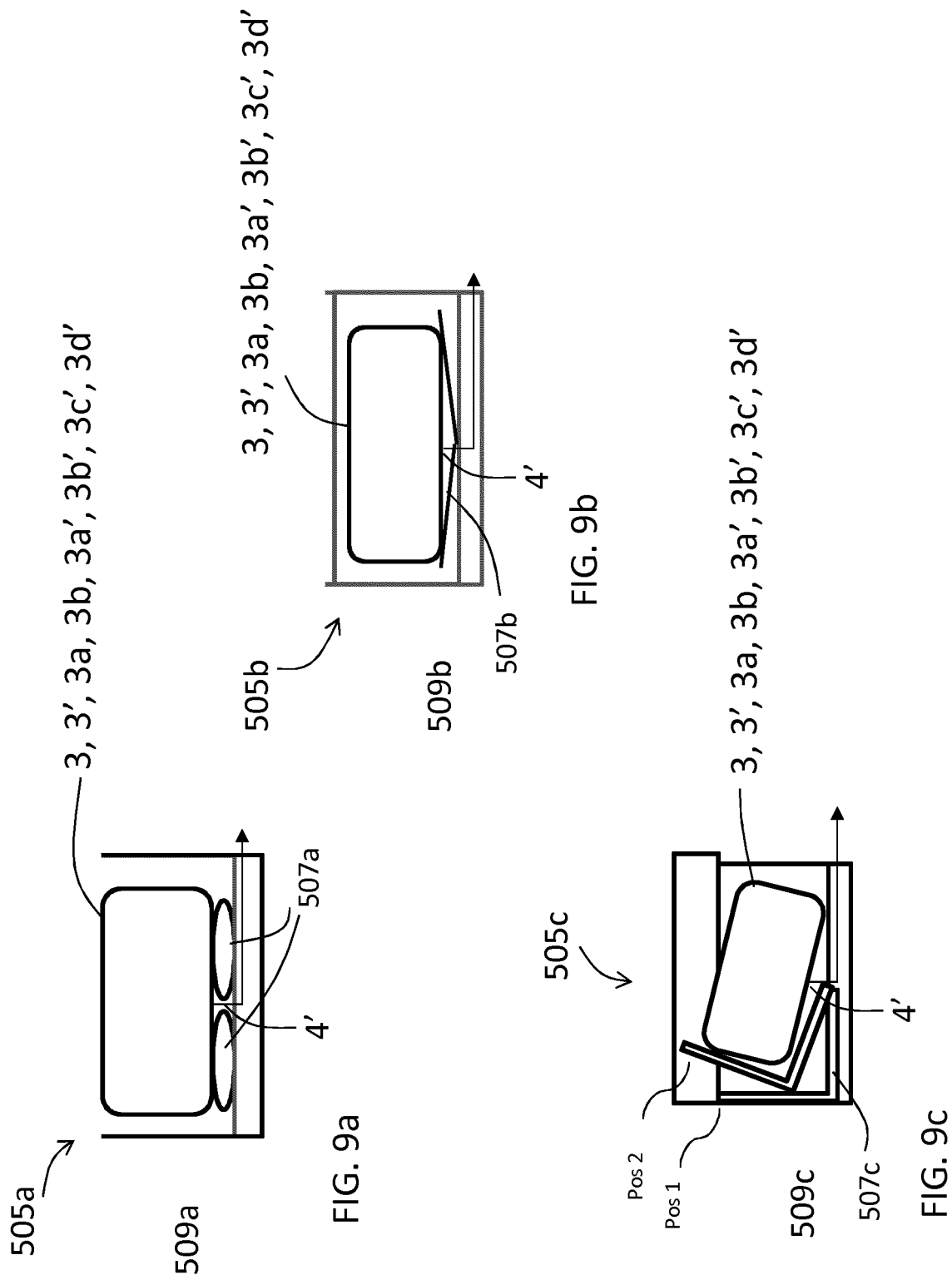

METHOD AND SYSTEM FOR TRANSFERRING SEPARATION RESIN

CROSS REFERENCE TO RELATED APPLICATIONS

This application claims the priority benefit of PCT/EP2018/052187 filed on Jan. 30, 2018, which claims priority benefit of Great Britain Application No. 1701576.9 filed on Jan. 31, 2017. The entire contents of which are hereby incorporated by reference herein.

TECHNICAL FIELD OF THE INVENTION

The present invention relates to a method and a system for transferring a separation resin from at least one first container to a second container. In particular, it relates to methods and systems useful in the packing of chromatography columns for manufacturing-scale separation of biopharmaceuticals.

BACKGROUND OF THE INVENTION

Separation media, also called separation resin, could be for example particle-formed chromatography media/resin. Such media/resins are typically used in the manufacturing of biopharmaceuticals to separate the biopharmaceutical from contaminants and impurities. The media could be for example resins based on natural or synthetic polymer particles or inorganic material, typically with a spherical particle shape and a particle size (e.g. a volume-weighted median particle diameter) in the 1-400 µm range, with a preference for 20-400 µm for resins used in large scale chromatography. These separation resins are supplied in a storage liquid, which can e.g. be an aqueous alcohol solution or a salt solution or a buffer. The resin particles quickly form a sediment cake in the storage container beneath a supernatant of storage liquid. The sediment cake is a relatively hard solid and to remove resin from the container, the container has to be shaken for a considerable time to suspend the resin so that it can be poured or otherwise transferred out of the container. For performing chromatography the separation resin needs to be provided into a chromatography column. For the transportation of the separation resin into for example a column the resin needs first to be suspended into a resin slurry mixture. The separation resin is normally suspended with a liquid, for example water, buffer or a solvent. This suspended resin is usually called resin slurry, media slurry, slurry or slurry of chromatography media/resin. When a chromatography column should be filled with resin slurry from one or more resin storage containers, an intermediate slurry tank is often used where the resin slurry is mixed into a homogenous mixture.

The transferring of separation resin from storage containers to a slurry tank can be handled in different ways. Sometimes the separation resin is poured into the slurry tank from the storage containers. However, the containers can be heavy and there may be a risk of spill and waste and biological contamination by operators. Chromatography media is very expensive so waste needs to be avoided and contamination must be prevented, particularly when the media is to be used for separation of parenteral biopharmaceuticals. Another method for transferring separation resin from a storage container to a slurry tank is to use some kind of transfer device, e.g. a membrane pump.

The handling and transferring of the separation resin is often at least in some steps an open process, i.e. the resin is exposed to ambient air and transferring means. This can introduce impurities and particles and biological vegetative contamination into the resin.

In the slurry tank the separation resin is mixed into a homogenous slurry mixture which then is transferred to the chromatography column. The whole amount of slurry needs to be transferred without interruption in order to avoid that the slurry starts to settle in the chromatography column before the packing procedure begins. When the slurry has been transferred to the column the packing process needs to get started as soon as possible while the slurry still is in suspended, homogenous form in order to achieve a uniformly packed bed.

SUMMARY

An object of the present invention is to provide an improved method and system for transferring separation resin between containers, typically in the packing of columns for manufacturing-scale separation of biopharmaceuticals.

This is achieved by a method according to embodiments disclosed herein and by a system according to embodiments disclosed herein.

Another object of the invention is to provide an improved container system to be used for the transferring of separation resin.

This is achieved in a container system according to embodiments disclosed herein.

According to one aspect of the invention a method is provided for transferring separation resin from at least one first container to a second container, wherein said first container is a deformable, single-use separation resin storage container, said method comprising the steps of:
- preparing the at least one first container by providing a deformable, single-use container comprising an outlet port with a predefined volume of separation resin in a storage solution;
- fluidizing the separation resin in the at least one first container to provide a resin slurry, said fluidizing being performed by mechanical interaction to the first container from an outside of the first container to provide a deformation of said first container;
- fluidically connecting the outlet port of the at least one first container to an inlet port of the second container;
- transferring separation resin from the at least one first container to the second container by generating a pressure difference between an interior of the second container and an interior of the first container where the pressure is lower in the second container.

According to another aspect of the invention a container system is provided wherein said container system comprises:
- at least one first container which is a deformable, single-use separation resin storage container comprising a predetermined volume of separation resin and a predetermined volume of storage solution, said first container further comprising an outlet port arranged for transferring the separation resin; and
- a mechanical interaction device provided in connection with an outside of the first container such that it can provide a deformation to said first container.

According to another aspect of the invention a system is provided for transferring separation resin between at least two containers, wherein said system comprises:
- at least one container system according to above, said container system comprising at least one first container;

a second container comprising an inlet port which is fluidically connected to the outlet port of said at least one first container; and a pressure difference generating device configured for transferring separation resin from the at least one first container to the second container by generating a pressure difference between an interior of the second container and an interior of the first container where the pressure is lower in the second container.

Hereby a method and a system for the transferring of a separation resin from at least one first container to a second container is achieved where the transferring of separation resin can be performed in a clean, closed system without exposing the separation resin to ambient air or a pump unit. The connections can be provided as disposable and pre-sterilized. Hereby a closed, safe transfer of separation resin between a single-use separation resin storage container and a separation device can be provided.

Furthermore, since the separation resin storage container is deformable and provided in contact with a mechanical interaction device which can provide a deformation to said first container and thereby fluidize settled separation media inside the separation media storage container an intermediate slurry tank can be omitted when separation media is transferred from a separation media storage container to for example a chromatography column. A direct and aseptic transfer of separation media is advantageous because there is a decreased risk of contamination and loss. Fluidizing the separation resin by deformation of the storage container is much more efficient than the traditional method of shaking the container, particularly for container sizes of above 1 L, such as 5 L-100 L or 5 L-50 L. The fluidization time is shortened significantly, less energy input is needed and the equipment can be more simple. Also, no external components such as agitators need to be introduced in the container, thus eliminating a potential contamination source.

Another object of the invention is to provide an improved method for aseptic packing of a chromatography column.

This is achieved by a method for aseptic packing of a chromatography column with a separation resin comprising the steps of:

filling a predetermined volume of separation resin and a volume of storage solution in a first container, said first container being a deformable, single-use container comprising an outlet port;

sterilizing the first container comprising the separation resin by gamma radiation;

sterilizing an interior of a chromatography column, said chromatography column being a second container;

aseptically connecting the first container to the second container;

fluidizing the separation resin in the at least one first container to provide a resin slurry, said fluidizing being performed by mechanical interaction to the first container from an outside of the first container to provide a deformation of said first container; and transferring separation resin from the at least one first container to the second container by generating a pressure difference between an interior of the second container and an interior of the first container where the pressure is lower in the second container.

Hereby the whole packing process in a chromatography column can be provided aseptic. Hereby there is no need for cleaning of tanks, tubing and pumps and there is less risk for contamination.

In one embodiment of the invention the step of transferring separation resin from the at least one first container to the second container comprises generating an under-pressure in the second container in relation to the pressure in the first container.

In one embodiment of the invention said second container is a separation device, such as a chromatography column and in particular a column for manufacturing-scale separation of a biopharmaceutical.

In one embodiment of the invention the step of fluidizing comprises fluidizing the separation resin into a free-flowing slurry. Hereby the separation resin can be transferred to the second container.

In one embodiment of the invention the step of preparing comprises preparing two or more first containers and the step of fluidically connecting the outlet port of the at least one first container to an inlet port of the second container comprises connecting the outlet port of each first container to a resin transfer manifold in series or in parallel and connecting the resin transfer manifold to the inlet of the second container. Hereby a resin transfer manifold can be used for the transfer of separation resin from more than one first containers. Hereby risk of contamination is decreased and the handling is facilitated.

In one embodiment of the invention the method further comprises the steps of sterilizing the at least one first container comprising separation resin by gamma radiation and sterilizing an interior of the second container before the step of fluidically connecting the outlet port of the at least one first container to an inlet port of the second container, wherein fluidically connecting is performed by aseptic connections. Hereby the whole process can be provided aseptic. Hereby there is no need for cleaning of tanks, tubing and pumps and there is less risk for contamination.

In one embodiment of the invention the at least one first container comprising separation resin and the second container are presterilized and the step of fluidically connecting is performed by aseptic connections.

In one embodiment of the invention said fluidizing is performed by manual interaction or by a mechanical interaction device from an outside of the first container to provide a deformation of said first container, wherein said mechanical interaction device is provided in a storage bin in which said first container is provided.

In one embodiment of the invention said fluidizing is performed by moving one or more movable bottom parts of a storage bin, inflating/deflating one or more inflatable air cushions provided in a storage bin or tilting the first container.

The pressure in the second container can suitably be at least 5 kPa, such as at least 10 kPa, 5-90 kPa or 5-70 kPa below the ambient atmospheric pressure. The pressure in the first container may e.g. be equal to the ambient atmospheric pressure or it may be less than about 5 kPa or 10 kPa above the ambient atmospheric pressure.

In one embodiment of the invention the step of allowing the under-pressure/vacuum in the second container to affect the content in the at least one first container comprises opening a valve provided in the transferring connection between the at least one first container and the second container, i.e. the transferring connection comprises at least one valve whereby opening of the valve allows under-pressure/vacuum provided to the second container to affect the content in the first container such that the separation resin initially provided in the first container is transferred to the second container through the transferring connection. Hereby opening and closing of the valve controls the transferring of separation resin from the first container to the second container.

In one embodiment of the invention the method further comprises the step of rinsing the at least one first container by transferring a rinsing solution through the at least one first container and further to the second container, said rinsing solution coming from a rinse bag connected to the at least one first container, said transferring of a rinsing solution being accomplished by the same under-pressure/vacuum as provided to the second container for transferring the separation resin. Hereby it can be assured that all separation resin initially provided in the first container is transferred to the second container. Waste of separation resin is avoided.

In one embodiment of the invention the step of rinsing the at least one first container comprises opening a rinsing valve provided in the connection between the at least one first container and the rinse bag to allow the under-pressure/vacuum provided to the second container to transfer rinsing solution from the rinse bag through the at least one first container and finally to the second container and closing the rinse valve when a suitable amount of rinsing solution has been transferred.

In one embodiment of the invention the method comprises connecting two or more first containers in series or in parallel to the second container allowing the content of all of the first containers to be transferred to the second container through one and the same transferring connection. Hereby only one transferring connection needs to be provided for transferring separation resin from more than one first containers. Hereby risk of contamination is decreased and the handling is facilitated.

In one embodiment of the invention the method further comprises the step of mixing the slurry in the second container by using a connected liquid supply system for fluidizing the slurry inside the second container. In one embodiment of the invention the second container is a chromatography column connected to a liquid supply system. Hereby a homogenized slurry can be achieved within the second container and a chromatography bed can be packed within the second container. Hereby an intermediate slurry tank can be avoided and the handling of slurry is simplified. Furthermore, the risk of contamination is decreased.

In one embodiment of the invention the step of providing a degree of vacuum/under-pressure to the second container by a vacuum production device/under-pressure generating device connected to the second container comprises controlling an adaptor provided in the second container.

In one embodiment of the invention the second container comprises a liquid distribution system at an inlet for the liquid supply system hereby improving a homogenization of the slurry provided by the fluidization.

In one embodiment of the invention the second container comprises an adaptor defining the internal volume of the second container together with a bottom and internal walls of the second container, which adaptor can be used as the vacuum production device/under-pressure generating device by raising it within the second container thus increasing the internal volume of the second container.

BRIEF DESCRIPTION OF THE DRAWINGS

FIG. 1 is a schematic drawing of a system according to one embodiment of the invention.

FIG. 2a is a schematic drawing of a system according to one embodiment of the invention in an initial phase of the process.

FIGS. 9a-c show schematically three different embodiments of a container system.

DETAILED DESCRIPTION OF THE INVENTION

Figure 2B:
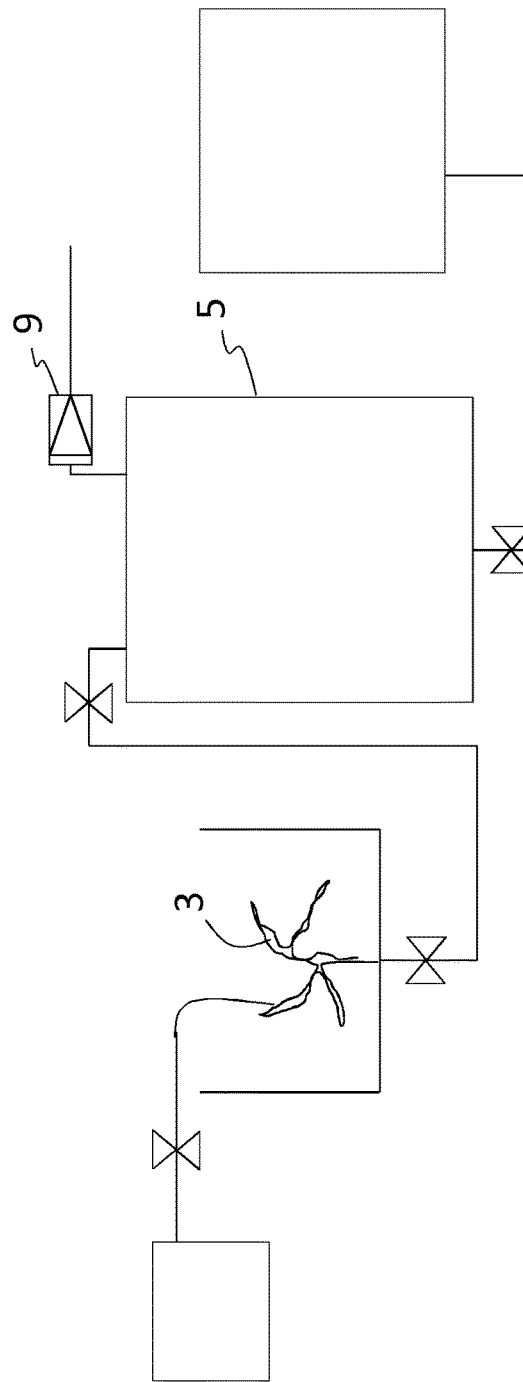
FIG. 2b is a schematic drawing of the same system as shown in FIG. 2a but in a later phase of the process.

FIG. 1 is a schematic drawing of a system 1 according to one embodiment of the invention. The system is a system for transferring a slurry of a separation resin/media, hereafter called a separation resin, a separation media, a resin slurry or only a slurry, between at least two containers. The separation resin can be a chromatography resin, often also called chromatography media.

A first container 3 and a second container 5 are shown in this embodiment. A transferring connection 7 is provided between the first and the second containers 3, 5. The first container 3 is a storage container for a separation resin, such as a slurry of chromatography resin. The first container can be a deformable single-use container. The first container can for example comprise at least one flexible section. In certain embodiments the first container 3 is a flexible disposable bag. The first container 3 can in these embodiments be made of for example a flexible plastic material, such as one or more plastic films or laminates. According to the invention the system further comprises a pressure difference generating device 9 configured for transferring separation resin from the at least one first container to the second container by generating a pressure difference between an interior of the second container and an interior of the first container where the pressure is lower in the second container. The pressure difference generating device 9 could be an under-pressure generating device 9 which is configured for generating an under-pressure in the second container in relation to the pressure in the first container. The pressure difference is used for transferring separation resin between the two containers. In one embodiment of the invention the under-pressure generating device is at least one vacuum production device 9 connected to the second container 5. Said vacuum production device 9 is arranged for providing a degree of under-pressure/vacuum in the second container 5 at least during a transferring of the slurry resin from the first container 3 to the second container 5. The vacuum production device 9 can be for example a vacuum pump or an ejector. The transferring connection 7 between the first container 3 and the second container 5 comprises according to one embodiment of the invention disposable connecting parts, such as pre-sterilized tubing and aseptic connectors. In another embodiment of the invention the transferring connection 7 comprises other tubing and connectors, not necessarily pre-sterilized. The separation resin initially provided in the first container 3 can be transferred from the first container 3 to the second container 5 through the transferring connection 7 by the under-pressure/vacuum provided to the second container 5 by the under-pressure generating device/vacuum production device 9.

The second container 5 is in one embodiment of the invention a slurry tank. A slurry tank is used as an intermediate step between a slurry storage container and a chromatography column. In the slurry tank the slurry can often be stirred into a homogenous slurry and it can be diluted to a wanted concentration. In another embodiment of the invention the second container 5 is a separation device such as a chromatography column and in particular a chromatography column for manufacturing-scale separation of a biopharmaceutical. This will be further described in relation to FIGS. 6, 8 and 9 below. In some cases where the chromatography column comprises a vacuum production device and no intermediate stirring and dilution is needed separation media could be transferred directly from a first container 3 into a chromatography column. Homogenization of the slurry could be performed inside the chromatography column itself which will be further described below.

Suitably the transferring connection 7 between the first container 3 and the second container 5 comprises at least one valve 11. Opening of the valve 11 will allow the pressure difference between the second container and the first container to affect also the content in the first container 3 such that the separation media which initially is provided in the first container 3 is transferred to the second container 5 through the transferring connection 7. Hereby a closed transferring of the separation media from the first container to the second container can be performed. The separation media will only pass through the transferring connection 7.

FIG. 2a is a schematic drawing of a system 21 according to one embodiment of the invention in an initial phase of the process and FIG. 2b is a schematic drawing of the same system 21 as shown in FIG. 2a but in a later phase of the process. The first and second containers 3, 5, the transferring connection 7 between them and the pressure difference generating device 9/vacuum production device 9 are given the same reference numbers as in the embodiment shown in FIG. 1 and the function of these parts are the same as described in relation to FIG. 1. The transferring connection 7 is in this embodiment shown to comprise a first valve 23a and a second valve 23b. The second valve 23b is provided close to the outlet of the first container 3 and can be suitable for inhibiting a resin plug which could hinder suction through the transferring connection to the second container 5. In this embodiment it is further shown how the second container 5 is connected to a chromatography column 25. In this embodiment the second container 5 is hereby not a chromatography column but rather a slurry tank. Furthermore, in this embodiment it is shown that the first container 3 is provided inside a rigid bin 27. If the first container 3 is a flexible bag such a rigid bin 27 is suitable for holding the first container 3 during transferring of the slurry to the second container 5.

Furthermore, in the embodiment shown in FIGS. 2A and 2B the system 21 further comprises a rinse bag 29 which is connected to the first container 3. Said rinse bag 29 comprises a rinsing solution, for example a buffer for rinsing the first container 3 when the separation media has been transferred to the second container 5. Said rinsing solution is transferred from the rinse bag 29 to the first container 3 by the same under-pressure/vacuum as provided to the second container 5 for transferring the slurry. A rinse valve 31 is provided in the connection between the rinse bag 29 and the at least one first container 3 such that rinsing solution is transferred form the rinse bag 29 to the first container 3 by the under-pressure/vacuum provided to the second container 5 by the under-pressure generating/vacuum production device 9 only when the valve 31 is open. Of course, also the valves 23a, 23b in the transferring connection 7 between the first container 3 and the second container 5 need to be open during the rinsing. Normally only a small amount of rinsing solution is needed for rinsing the first container 3. An operator can open and close the rinse valve 31 manually and the operator can normally see how much rinsing solution is needed for the rinsing and thus how long time the rinse valve needs to be open. However, an automated control of the opening and closing of the rinse valve 31 can also be provided.

In FIG. 2B the system 21 of FIG. 2A is shown in a later stage of the process when the first container 3 has been emptied. Because the first container 3 in this embodiment is a flexible bag the bag will be emptied and compacted by the under-pressure/vacuum, shown in FIG. 2B.

Figure 3:
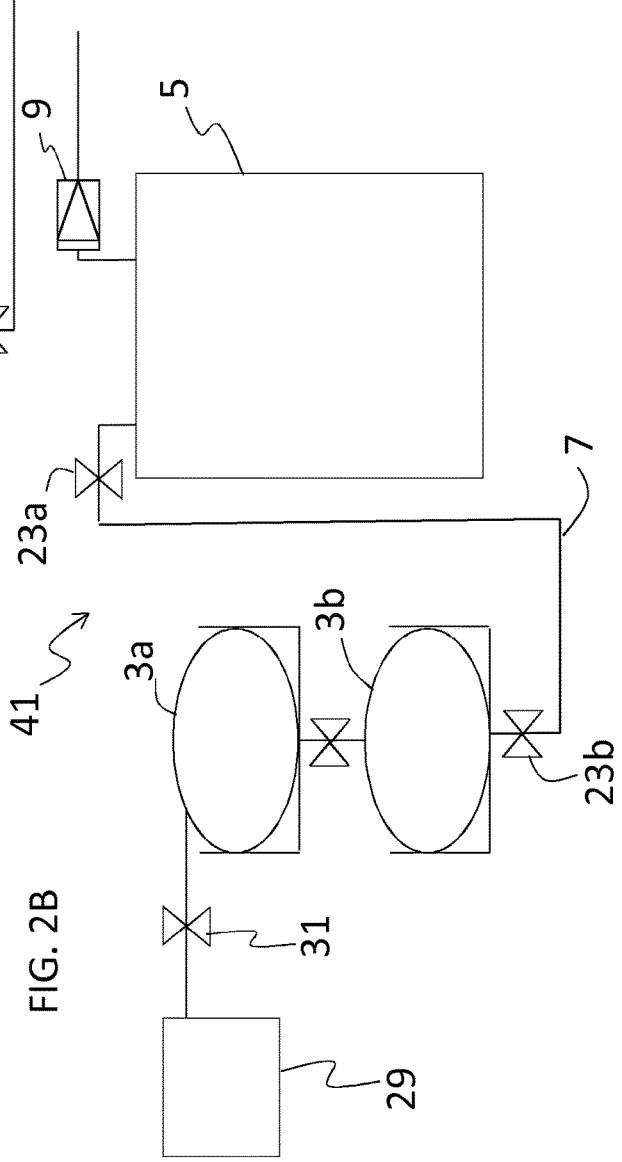
FIG. 3 is a schematic drawing of a system according to one embodiment of the invention.

FIG. 3 is a schematic drawing of a system 41 according to one embodiment of the invention. The rinse bag 29, the rinse valve 31 and the second container 5 corresponds to the same components as described in relation to the embodiment of FIGS. 2A and B (however in this embodiment the second container 5 can be a slurry tank or a chromatography column as in FIG. 1) and keep the same reference numbers. In this embodiment however there are more than one first container 3a, 3b provided. Here two first containers 3a, 3b are shown connected in series. They could as well be connected in parallel. A transferring connection 7 is provided between the second container 5 and the set of first containers 3a, 3b. If the first containers as in this example are connected in series the connection 7 is provided from the last one of the first containers 3b in the series. A reason for connecting more than one first containers 3 at the same time for transferring of separation resin to the second container 5 is that often these storage containers for separation media (first container) are small compared to a slurry tank or chromatography column (second container). By connecting the first containers to each other (in series or in parallel) all of them can be emptied into the second container at the same time using one and the same transferring connection 7. If instead the transferring connection 7 needs to be set up for each first container 3 to be emptied into the second container 5 there may be an increased risk for contamination.

With this invention a closed slurry transferring system has been provided. Because disposable parts and aseptic connections can be used and because the separation resin is not subjected to ambient air during the transferring cleaning validation of the transfer system can be avoided. Furthermore, the separation resin will not be in contact with a pumping device (which would be the case in some prior art). This will provide the possibility to use only disposable clean parts for the transferring.

Figure 4:
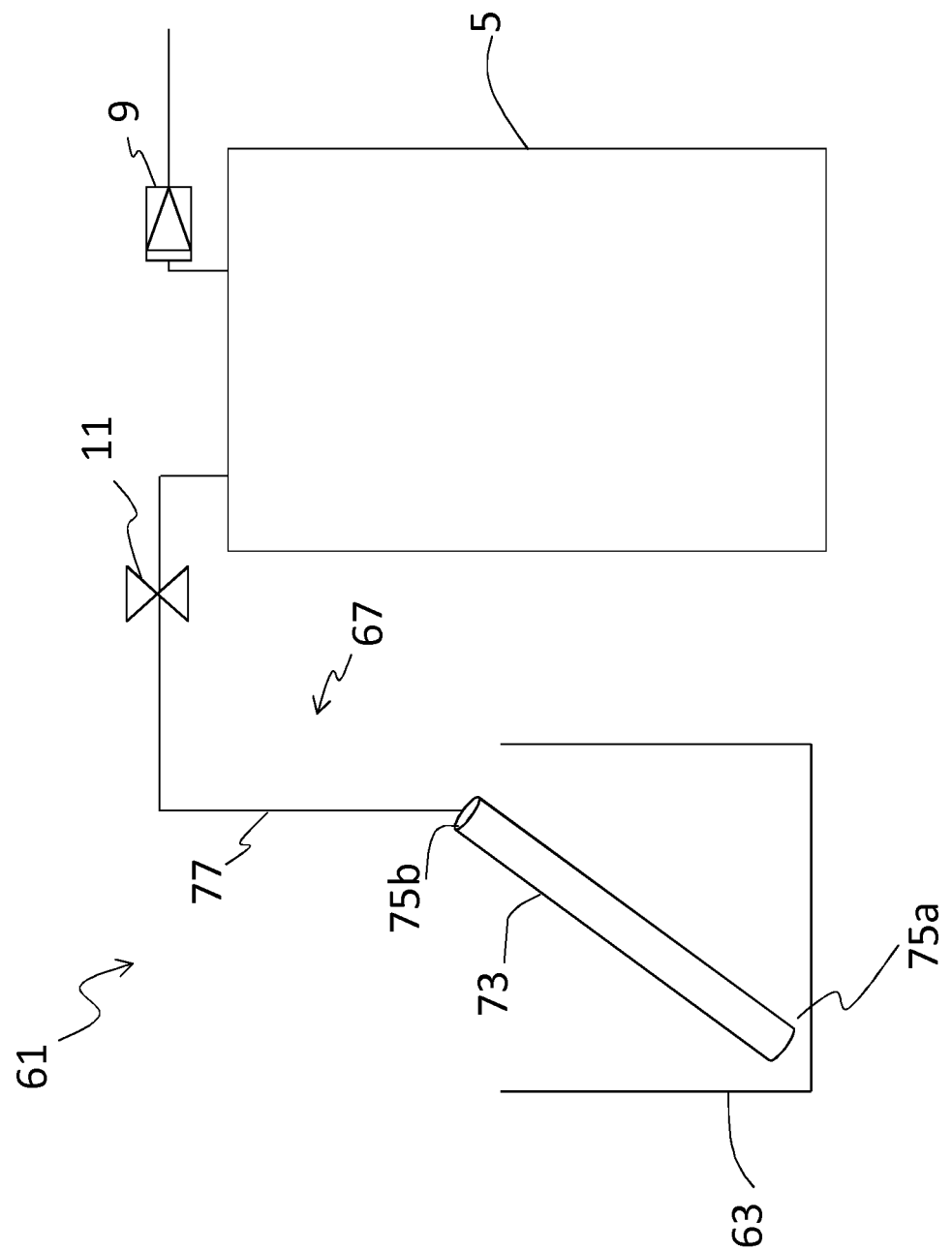
FIG. 4 is a schematic drawing of a system according to one embodiment of the invention.

FIG. 4 is a schematic drawing of a system 61 according to one embodiment of the invention. In this system 61 a transferring connection 67 between a first container 63 and a second container 5 comprises a disposable hollow rod 73 with a first end 75a of the hollow rod 73 arranged for pointing down into the first container 63 and a second end 75b of the hollow rod 73 arranged to be connected by tubing 77 and connectors, possibly disposable, pre-sterilized tubing and aseptic connectors, to the second container 5. In this embodiment the first container 63 need not be a flexible bag but can as well be a rigid storage container for slurry. The principle is however the same: a vacuum production device 9 connected to the second container 5 produces a degree of vacuum in the second container 5, which vacuum is used to transfer slurry form the first container 63 to the second container 5. A valve 11 in the transferring connection 67 between the first container 63 and the second container 5 needs to be opened when the slurry is transferred.

Figure 5:
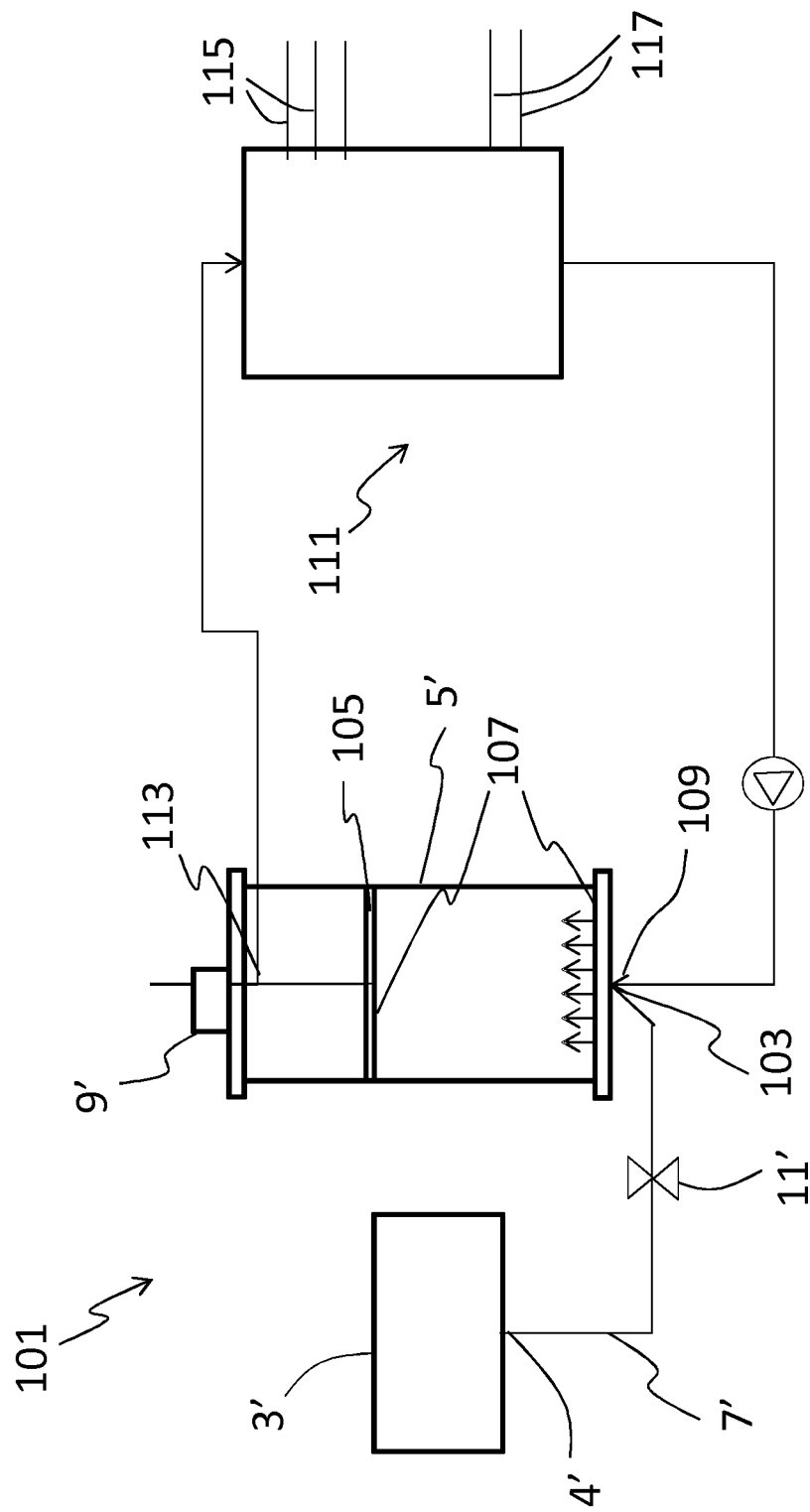
FIG. 5 is a schematic drawing of a system according to one embodiment of the invention.

FIG. 5 is a schematic drawing of a system 101 according to one embodiment of the invention. This is the same system as described in FIG. 1 but including more details of the second container 5'. In this embodiment of the invention the second container 5' is a separation device such as a chromatography column. A first container 3' is here a deformable, single-use separation resin storage container and it comprises an outlet port 4' which is connected to a slurry inlet 103 of the second container 5'. The slurry inlet 103 is here shown provided in a bottom part of the second container 5'. In this embodiment of the invention the second container 5' comprises also an adaptor 105 commonly used for packing a chromatography bed by compressing the slurry. The adaptor 105 can be controlled to move up and down inside the chromatography column (second container) 5' and defines together with the inner walls of the second container 5' the internal volume of the chromatography column 5'. A pressure difference generating device 9'/an under-pressure generating device 9'/vacuum production device 9' is provided to the second container 5'. This could either be the control of the adaptor position. When lifting the adaptor in the closed internal volume of the second container 5' an under-pressure will be provided inside the second container 5'. Alternatively, the vacuum production device 9' could be a vacuum pump or ejector as described above. The second container 5' comprises in this embodiment two liquid distribution plates and filters 107. The liquid distribution plates are provided for distributing sample and buffer over the whole cross section area of the second container and the filters are provided for keeping the chromatography media inside the column. One liquid distribution plate and filter is provided at a bottom of the column and one is provided to the adaptor 105. The inlet 103 for the separation resin slurry allows the separation resin to pass the liquid distribution plate and the filter 107. A separate sample and buffer inlet 109 is also provided to a bottom part of the second container 5'. The sample and buffer inlet 109 is connected to a liquid supply system 111. The liquid supply system 111 is further connected to an outlet 113 from the second container 5' provided through the adaptor 105. The liquid supply system comprises inlets 115 and outlets 117 for further connection to different samples and buffers to be provided to the second container 5' and to different collection devices for collecting sample outlet form the chromatography system.

Separation resin can be provided from the first container 3' to the second container 5' by use of a pressure difference/under-pressure/vacuum in the same way as described above in relation to the previously described embodiments, for example by opening the valve 11' and lifting the adaptor 105 by the pressure difference generating device 9'/under-pressure generating device 9'/vacuum production device 9' (which in this example can be a motor for lifting the adaptor). If further homogenization of the separation resin slurry is needed before a packing procedure starts buffer, solution or water can be fluidized through the second container 5' and thus through the slurry by the use of the liquid supply system 111 and sample and buffer inlet 109 and outlet 113. This will cause the slurry to be mixed and homogenized.

One or more separation resin storage bags (first containers 3'), which possibly are prefilled, flexible and pre-sterilized, can be connected by pre-sterilized, disposable tubing to the chromatography column (second container 5'). The separation resin slurry can be provided to the chromatography column without any risk for contamination and if needed further slurry homogenization can be provided inside the column itself. Because of the homogenization step inside the second container 5' it is not crucial to fill the separation resin slurry in one continuous process. Furthermore, a rinse bag 29 as described in relation to the previous embodiments can be provided also to this embodiment. This is also shown in the embodiment described below in relation to FIG. 6.

Figure 6:
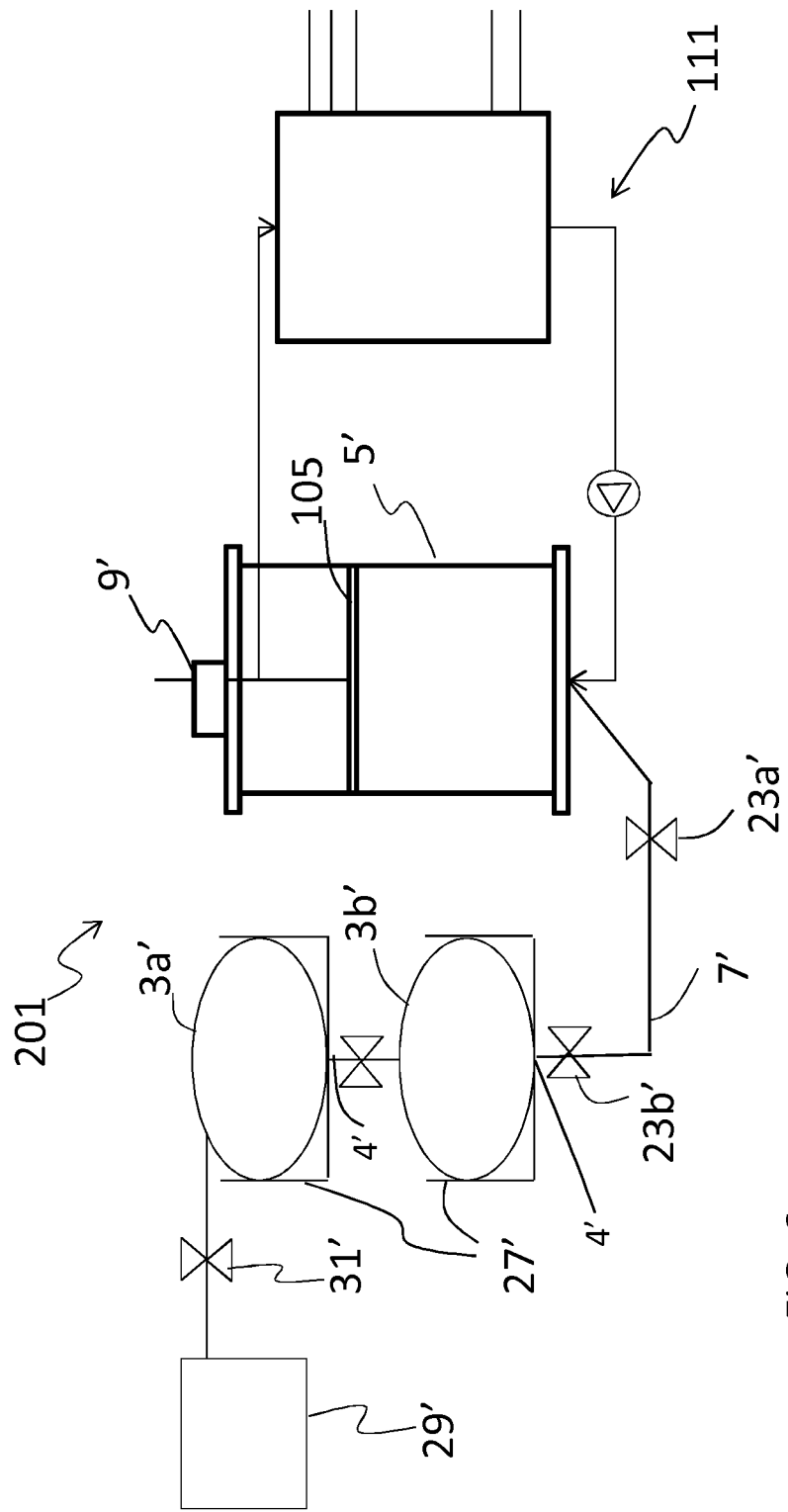
FIG. 6 is a schematic drawing of a system according to one embodiment of the invention.

FIG. 6 is a schematic drawing of a system 201 according to one embodiment of the invention. The second container 5' is also in this embodiment a chromatography column as described above in relation to FIG. 5. Here two first containers 3a', 3b' are provided connected in series in the same way as described in relation to FIG. 3. They could also be connected in parallel or be more than two. This is further described in relation to FIGS. 8 and 9 below. The transferring connection 7' is in this embodiment shown to comprise a first valve 23a' and a second valve 23b' just as described in relation to FIGS. 2 and 3. Furthermore, in this embodiment it is shown that the first containers 3a', 3b' are provided inside rigid bins 27'. If the first containers 3a', 3b' are flexible bags such a rigid bin 27' is suitable for holding the first containers 3a', 3b' during transferring of the separation resin to the second container 5'. Such a rigid bin can also comprise a mechanical interaction device as will be further described below in relation to FIGS. 10*a-c*.

The system 201 further comprises a rinse bag 29' which is connected to the first containers 3a', 3b'. Said rinse bag 29' comprises a rinsing solution, for example a buffer for rinsing the first containers 3a', 3b' when the slurry has been transferred to the second container 5'. Said rinsing solution is transferred from the rinse bag 29' to the first containers 3a', 3b' by the same under-pressure/vacuum as provided to the second container 5' for transferring the separation resin. A rinse valve 31' is provided in the connection between the rinse bag 29' and the at least one first containers 3a', 3b' such that rinsing solution is transferred form the rinse bag 29' to the first containers 3a', 3b' by the under-pressure/vacuum provided to the second container 5' by the under-pressure generation device/vacuum production device 9' only when the valve 31' is open. Of course also the valves 23a', 23b' in the transferring connection 7' between the first containers 3a', 3b' and the second container 5' need to be open during the rinsing. Normally only a small amount of rinsing solution is needed for rinsing the first containers 3a', 3b'. In one embodiment of the invention an air sensor can be provided to the inlet to the second container. When the second container is a chromatography column air should suitably be avoided to be transferred into the chromatography column. A liquid supply system 111 is connected to the second container 5' in the same way as described above in relation to FIG. 5. Hereby the separation resin slurry can be homogenized by flowing a buffer, solution or water through the slurry inside the second container 5' before the slurry later is packed. Furthermore, the second container 5' can comprise adaptor 105 and filter and distribution system 107 as described above in relation to FIG. 5.

Figure 7:
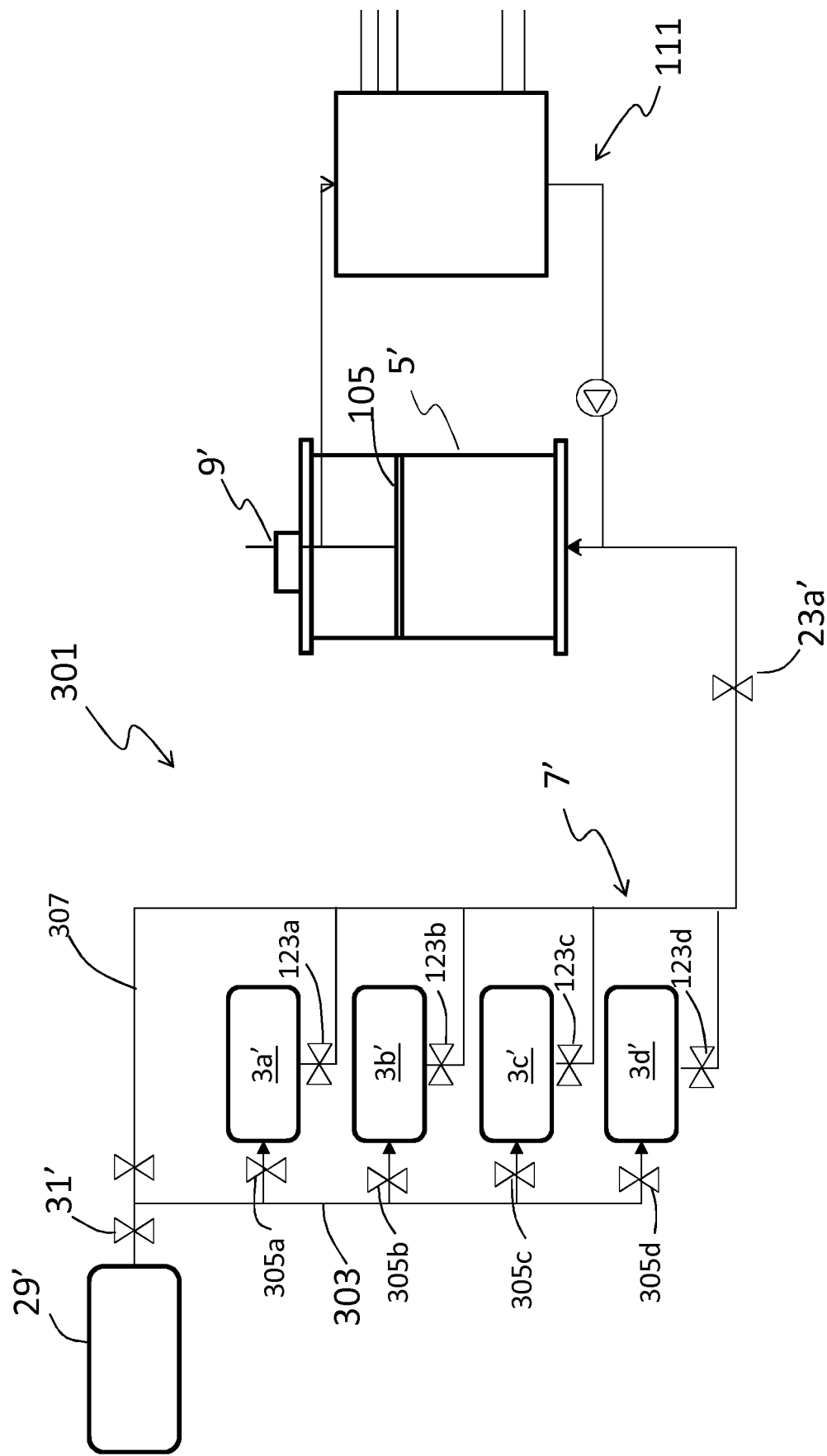
FIG. 7 is a schematic drawing of a system according to one embodiment of the invention.

FIG. 7 is a schematic drawing of a system 301 according to one embodiment of the invention. The system is similar to the system described in relation to FIG. 6 and therefore also most of the reference numbers are the same. The second container 5' is a separation device such as a chromatography column. Four first containers 3a', 3b', 3c', 3d' are shown in the system 301. However, the number of first containers could of course be varied. They are here connected in parallel to the second container 5'. A transferring connection 7' connects the outlets 4' from the first containers to the inlet of the second container. Valves are suitably provided; both a first valve 23a' as described above and also one valve 123a,b,c,d for the outlets of each first container 3a',3b',3c', 3d'. The transferring connection 7' can be provided as a resin transfer manifold. Furthermore, a rinse bag 29' is provided connected to inlets of the first containers through a rinse valve 31' in the same way as described above in relation to FIG. 6. A rinse manifold 303 can be provided connecting the rinse bag 29' with inlets of each first container for delivering rinse solution to each of the first containers. Suitably also a second rinse valves 305a,b,c,d is provided for allowing control of rinse solution into each of the first containers. Furthermore, a bypass rinse connection 307 can be provided connecting the rinse bag 29' directly to the second container 5'. This is only optionally and can be used as a final rinse and/or for priming.

The second container 5' comprises a pressure difference generating device 9', for example an under-pressure generating device 9'. Hereby a pressure inside the second container can be changed by this pressure difference generating device 9'. If the pressure is lower inside the second container 5' than inside the at least one first container this pressure difference can be used for transferring the separation resin between the containers. In one embodiment of the invention the under-pressure generating device is a vacuum production device 9' as described above. As also described above an adaptor 105 provided inside the second container 5' can be moved for generating an under-pressure. In another embodiment of the invention a pressure difference between the first and second container can be provided by other means, for example by squeezing the first container.

Furthermore, a liquid supply system 111 is provided in the system 301 in the same way as described in relation to FIGS. 5 and 6. This liquid supply system can be used for fluidizing the separation resin slurry inside the second container.

Figure 8:
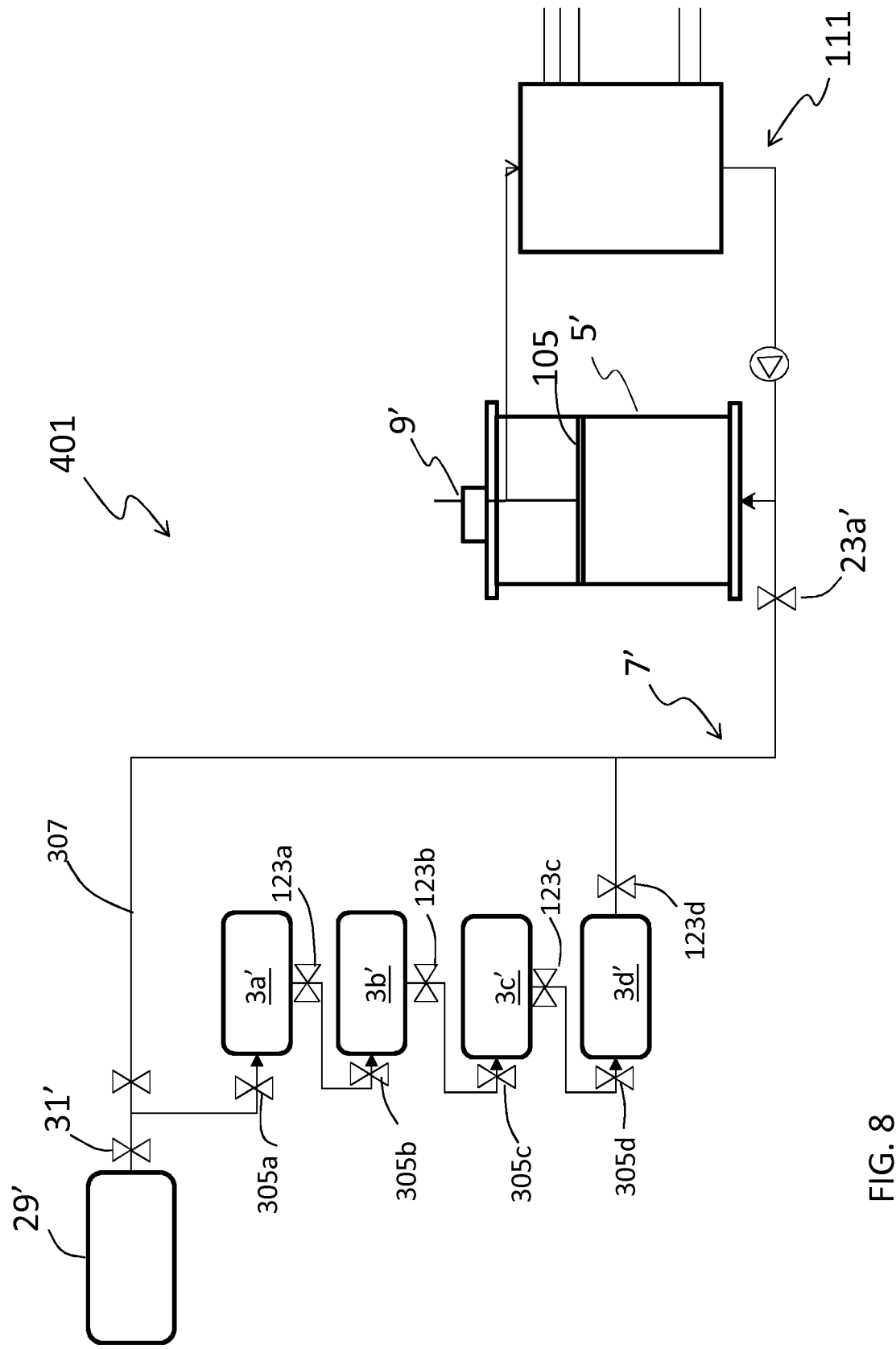
FIG. 8 is a schematic drawing of a system according to one embodiment of the invention.

FIG. 8 is a schematic drawing of a system 401 according to one embodiment of the invention. Also this system is similar to the system described in relation to FIGS. 6 and 7 and therefore also most of the reference numbers are the same. The only difference from the system 301 as described in relation to FIG. 7 is that the first containers 3a',b',c',d' are connected in series instead of in parallel. The number of first containers is here four but can of course be varied. Valves can be provided both in connection with the inlet and the outlet of each first container as in the embodiment described in relation to FIG. 7. The valves are also given the same numbers as in FIG. 7. The difference is the fluid connections between the first containers 3a'b',c',d' connecting them in series with the first one 3a' connected to the rinse bag 29' and the last one 3d' connected to the second container 5'. Hereby the content of all the first containers provided in the system 401 will be emptied one after each other and finally rinse solution can be flowed through the series of first containers for assuring all separation resin will be transferred to the second container. Furthermore, a bypass rinse connection 407 can optionally be provided connecting the rinse bag 29' directly to the second container 5'.

A reason for connecting more than one first containers at the same time for transferring of separation resin to the second container is that often these storage containers for separation media (first container) are small compared to a slurry tank or chromatography column (second container). By connecting the first containers to each other (in series or in parallel) all of them can be emptied into the second container at the same time using one and the same transferring connection. If instead the transferring connection needs to be set up for each first container to be emptied into the second container there may be an increased risk for contamination.

With this invention a closed separation resin transferring system has been provided. Because disposable parts and aseptic connections can be used and because the separation resin is not subjected to ambient air during the transferring cleaning validation of the transfer system can be avoided. Furthermore, the separation resin will not be in contact with a pumping device (which would be the case in some prior art). This will provide the possibility to use only disposable clean parts for the transferring.

FIGS. 9a-c show schematically three different embodiments of a container system 505a, 505b, 505c according to the invention. The container system 505a, 505b, 505c, comprises at least one first container 3,3', 3a-c, 3a'-d' as described above. The first container is a deformable, single-use separation resin storage container comprising a predetermined volume of separation resin and a predetermined volume of storage solution. The first container comprises further an outlet port 4' arranged for transferring the separation resin. The container system 505a, 505b, 505c comprises furthermore a mechanical interaction device 507a, 507b, 507c provided in connection with an outside of the first container 3, 3', 3a-c, 3a'-d' such that it can provide a deformation to said first container. This deformation needs to be substantial in order to provide fluidization to some degree of the separation resin within the first container. The fluidization needs to be to a degree such that the separation resin can be transferred to the second container, i.e. such that a free-flowing slurry is provided. This may require a deformation of at least 5% of the volume of the first container or in another embodiment at least 10% of the volume of the first container. This may also require repeated deformations of the first container, for example at least 5 deformations or in another embodiment at least 10 deformations. Deformation is suitably provided to a lower part of the first container, where lower refers to the part of the first container closest to the ground because due to gravity a cake of settled separation resin will be provided there.

Figure 10B:
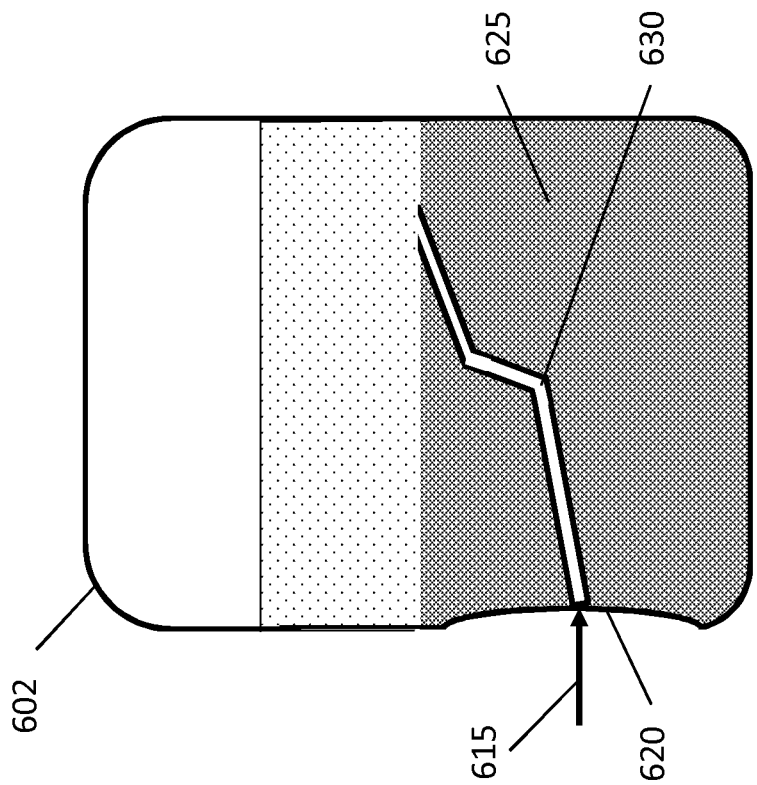
FIG. 10b shows schematically how separation resin inside a deformable container can be fluidized by mechanical interaction from outside the container according to the invention.
Figure 10A:
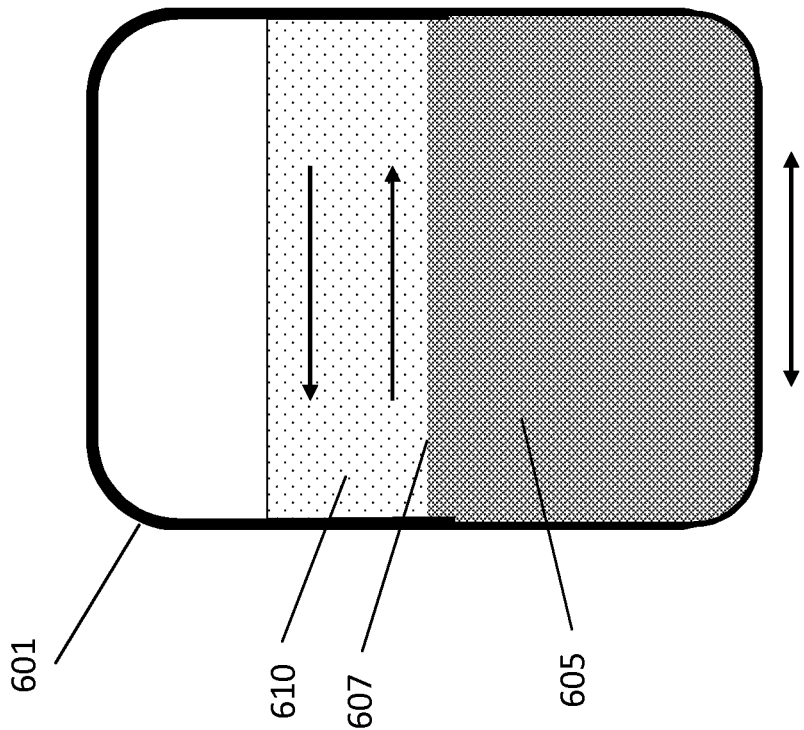
FIG. 10a shows schematically how separation resin inside a rigid container is agitated.

In the embodiments as described in relation to FIGS. 9a-c the mechanical interaction device 507a-c is provided in a storage bin 509a-c in which said first container can be provided. Such a storage bin is suitably a rigid storage bin in which one or more deformable first containers can be stored and transported. The mechanical interaction device 507a-c will be used for deforming the first container in order to fluidize the separation resin provided inside the first container. FIG. 10a shows schematically how separation resin inside a rigid container 601 is fluidized by agitating the container through shaking. A gradual erosion will take place of the cake of settled separation resin 605 from a top layer 607 as liquid phase 610 above the cake is agitated by shaking of the container. This requires intense shaking for a lengthy period of time. FIG. 10b shows schematically how separation resin inside a deformable container 602, e.g. a flexible bag, according to the invention can be fluidized by mechanical interaction 615 from outside the container according to the invention. A pressure 615 applied from outside the first container 602 and causing a deformation of a flexible container wall 620 will be directly transformed to disintegration of the separation resin cake 625, as illustrated by the formation of a crack 630, thanks to the deformable container. Hereby rapid fluidization of the separation resin will be facilitated.

In the container system 505a of FIG. 9a the mechanical interaction device 507a is one or more inflatable air cushions provided inside the rigid storage bin 509a, for example in the bottom of the storage bin 509a. When air is inflated/deflated into said air cushions the deformable first container provided inside the storage bin 509a will be deformed and a settled cake of separation resin inside the first container will start to be fluidized. Fluidizing in this step of the procedure needs only to be to an extent such that it is possible to transfer the separation resin, i.e. it is often not necessary to provide a completely fluidized separation resin but only enough fluidized for allowing the transferring. Further fluidizing could later be provided inside the second container as described above. Therefore, the term fluidizing in this text and in the claims will not necessarily mean a specific degree of fluidization.

In the container system 505b of FIG. 9b the mechanical interaction device 507b is one or more movable parts of the storage bin 509b. This could for example be one or more movable parts of a bottom of the storage bin. When these one or more movable parts are moved the first container will be deformed as described above.

In the container system 505c of FIG. 9c the mechanical interaction device 507c is a part of the storage bin 509c which can be tilted, i.e. the first container provided inside the storage bin can be tilted in order to provide a deformation to the first container.

In another embodiment of the invention the mechanical interaction device is a manual interaction provided to the first container, for example a person lifting a part of the first container or a person squeezing the first container. Possibly the first container can be provided hanging for facilitating the deformation of the first container. As discussed above a deformation of for example at least 5% of the volume of the first container or in another embodiment at least 10% of the volume of the first container may be required for achieving enough fluidization of the separation resin. This may require repeated deformations of the first container, for example at least 5 deformations or in another embodiment at least 10 deformations. The deformation to the first container can suitably be provided to a lower part of the first container, where lower refers to a part of the container closer to the ground because due to gravity a cake of settled separation resin will be provided there.

Figure 11:
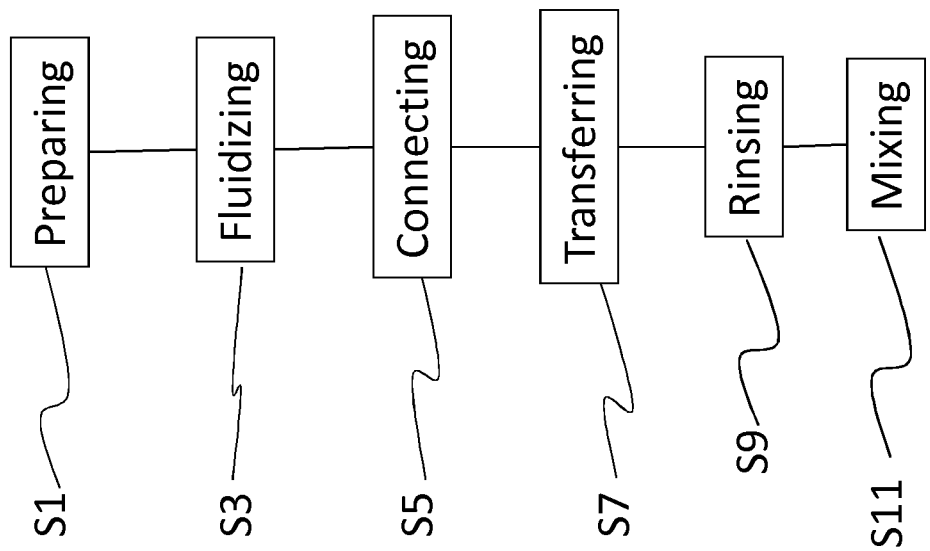
FIG. 11 is a flow chart of a method according to one embodiment of the invention.

FIG. 11 is a flow chart of a method for transferring a slurry of a separation resin from at least one first container 3; 3'; 3a, 3b; 3a', 3b', 3c', 3d' to a second container 5, 5' according to one embodiment of the invention. The method steps are described below:

S1: Preparing the at least one first container by providing a deformable, single-use container comprising an outlet port with a predefined volume of separation resin in a storage solution.

S3: Fluidizing (at least to some degree) the separation resin in the at least one first container to provide a resin slurry, said fluidizing being performed by mechanical interaction to the first container from an outside of the first container to provide a deformation of said first container. As discussed above a substantial deformation of the first container would be required for providing a suitable fluidization. This could be for example that at least 5% of the volume of the first container is deformed or at least 10% of the volume of the container is deformed. Furthermore repeated deformations may be required, for example at least 5 or at least 10 deformations.

S5: Fluidically connecting the outlet port 4' of the at least one first container 3; 3'; 3a, 3b; 3a', 3b' to an inlet port of the second container 5; 5'. This can be done by a transferring connection 7; 7'. The transferring connection 7; 7' comprises in one embodiment disposable connecting parts, which could be pre-sterilized tubing and aseptic connectors. In another embodiment the transferring connection 7; 7' comprises other, non-sterile tubing and connectors. The transferring connection 7' can be a resin transfer manifold 7' connecting the outlet from a number of first containers 3a', 3b', 3c' etc to the inlet of the second container 5'. The order of steps S3 and S5 can be reversed, i.e. the step of fluidizing S3 can instead be performed after the step of fluidically connecting S5.

S7: Transferring separation resin from the at least one first container to the second container by generating a pressure difference between an interior of the second container and an interior of the first container where the pressure is lower in the second container. Such a pressure difference can be provided for example by a pressure difference generating device as described above, for example in the form of an under-pressure generating device/vacuum production device as also described above. However other alternatives, such as squeezing the first container is also possible. Raising an adaptor provided inside the second container has also been described as an alternative above.

The step of preparing, S1, comprises in one embodiment preparing two or more first containers and the step of fluidically connecting, S5, the outlet port of the at least one first container to an inlet port of the second container comprises in one embodiment connecting the outlet port of each first container to a resin transfer manifold in series or in parallel and connecting the resin transfer manifold to the inlet of the second container.

The method can in one embodiment of the invention further comprise the steps of sterilizing the at least one first container comprising separation resin by gamma radiation and sterilizing an interior of the second container before the step of fluidically connecting the outlet port of the at least one first container to an inlet port of the second container, wherein fluidically connecting is performed by aseptic connections.

Said mechanical interaction to the first container from an outside of the first container to provide a deformation of said first container can be performed by manual interaction or by a mechanical interaction device provided in a storage bin in which said first container is provided.

By allowing the under-pressure/vacuum in the second container 5; 5' to affect the content in the at least one first container 3; 3'; 3a, 3b; 3a', 3b'; 63 through the transferring connection 7; 7' the separation resin which initially is provided in the at least one first container 3; 3'; 3a, 3b; 3a', 3b'; 63 is transferred to the second container 5; 5' through the transferring connection 7; 7' without the separation resin being in contact with the vacuum production device 9; 9' during the transfer.

In one embodiment of the invention the step of allowing the under-pressure/vacuum provided in the second container 5; 5' to affect the content in the at least one first container 3; 3'; 3a, 3b; 3a', 3b'; 63 comprises opening a valve 11; 11' provided in the transferring connection 7; 7' between the at least one first container 3; 3'; 3a, 3b; 3a', 3b'; 63 and the second container 5; 5'.

In one embodiment of the invention the method further comprises the optional step of:

S9: Rinsing the at least one first container 3; 3'; 3a, 3b; 3a', 3b'; 63 in order to assure that substantially all separation resin will be transferred to the second container 5; 5'. The rinsing being accomplished by transferring a rinsing solution, which could be for example a buffer, through the at least one first container 3; 3'; 3a, 3b; 3a', 3b'; 63 and further to the second container 5; 5'. Said rinsing solution coming from a rinse bag 29; 29' connected to the at least one first container 3; 3'; 3a, 3b; 3a', 3b'; 63 and said transferring of a rinsing solution being accomplished by the same under-pressure/vacuum as provided to the second container 5; 5' for transferring the separation resin.

Suitably the step of rinsing the at least one first container 3; 3'; 3a, 3b; 3a', 3b'; 63 comprises opening a rinsing valve 31; 31' provided in the connection between the at least one first container 3; 3'; 3a, 3b; 3a', 3b'; 63 and the rinse bag 29; 29' to allow the under-pressure/vacuum provided to the second container 5; 5' to transfer rinsing solution from the rinse bag 29; 29' through the at least one first container 3; 3'; 3a, 3b; 3a', 3b'; 63 and finally to the second container 5; 5' and closing the rinse valve when a suitable amount of rinsing solution has been transferred.

In one embodiment of the invention the method comprises connecting two or more first containers 3a, 3b; 3a', 3b' in series or in parallel to the second container 5; 5' allowing the content of all of the first containers 3a, 3b; 3a', 3b' to be transferred to the second container 5; 5'.

In one embodiment of the invention the method further comprises the optional step of:

S11: Mixing the separation resin slurry in the second container 5; 5'. By mixing the separation resin slurry the slurry will be homogenized and can be packed into a chromatography bed. Hereby the use of an intermediate slurry tank can be avoided. The mixing of the slurry in the second container 5; 5' can be performed by fluidizing the slurry, for example from below as shown in FIGS. 5-8. A connected liquid supply system could provide buffer or water to the second container 5, 5' and hereby the slurry can be mixed and homogenized.

According to the invention a method for aseptic packing of a chromatography column with a separation resin is also provided. Said method comprises the steps of:

filling a predetermined volume of separation resin and a volume of storage solution in a first container, said first container being a deformable, single-use container comprising an outlet port;

sterilizing the first container comprising the separation resin by gamma radiation;

sterilizing an interior of a chromatography column, said chromatography column being a second container;

aseptically connecting the first container to the second container;

fluidizing, at least to some degree, the separation resin in the at least one first container to provide a resin slurry, said fluidizing being performed by mechanical interaction to the first container from an outside of the first container to provide a deformation of said first container; and transferring separation resin from the at least one first container to the second container by generating a pressure difference between an interior of the second container and an interior of the first container where the pressure is lower in the second container.

The transferring of the separation resin from the first container to the second container can be performed according to the method as described above in relation to FIG. 11.

Whilst different embodiments have been described above, and illustrated, it will be apparent to the skilled person that additions, modifications, or deletions could be applied to those embodiments without departing from the invention as claimed.

The invention claimed is:

1. A method for transferring separation resin from at least one first container to a second container, wherein said first container is a deformable, single-use separation resin storage container, and wherein said second container is a separation device, said method comprising the steps of:

preparing the at least one first container by providing a deformable, single-use container comprising an outlet port with a predefined volume of separation resin in a storage solution;

fluidizing the separation resin into a free flowing slurry in the at least one first container to provide a resin slurry, said fluidizing being performed by mechanical interaction to the first container from an outside of the first container to provide a deformation of said first container;

fluidically connecting the outlet port of the at least one first container to an inlet port of the second container; and transferring separation resin from the at least one first container to the second container by generating an under-pressure between an interior of the second container in relation to a pressure in an interior of the first container.

2. The method according to claim 1, wherein the step of preparing comprises preparing two or more first containers and the step of fluidically connecting the outlet port of the at least one first container to an inlet port of the second container comprises connecting the outlet port of each first container to a resin transfer manifold in series or in parallel and connecting the resin transfer manifold to the inlet of the second container.

3. The method according to claim 1, further comprising the steps of sterilizing the at least one first container comprising separation resin by gamma radiation and sterilizing an interior of the second container before the step of fluidically connecting the outlet port of the at least one first container to an inlet port of the second container, wherein fluidically connecting is performed by aseptic connections.

4. The method according to claim 1, wherein the at least one first container comprising separation resin and the second container are presterilized and the step of fluidically connecting is performed by aseptic connections.

5. The method according to claim 1, wherein said fluidizing is performed by a mechanical interaction device from an outside of the first container to provide a deformation of said first container, wherein said mechanical interaction device is provided in a storage bin in which said first container is provided.

6. The method according to claim 5, wherein said fluidizing is performed by moving one or more movable bottom parts of a storage bin, inflating/deflating one or more inflatable air cushions provided in a storage bin or tilting the first container.

7. The method according to claim 1, wherein the step of transferring separation resin from the at least one first container to the second container comprises:

providing a degree of vacuum/under-pressure to the second container by a vacuum production device connected to the second container;

allowing the vacuum/under-pressure in the second container to affect the content in the at least one first container through a transferring connection which is fluidically connecting the at least one first container with the second container, such that the separation resin initially provided in the at least one first container is transferred to the second container through the transferring connection.

8. The method according to claim 7, wherein the step of allowing the under-pressure/vacuum in the second container to affect the content in the at least one first container comprises opening at least one valve provided in the transferring connection between the at least one first container and the second container.

9. The method according to claim 1, further comprising the step of:

rinsing the at least one first container by transferring a rinsing solution through the at least one first container and further to the second container, said rinsing solution coming from a rinse bag connected to the at least one first container, said transferring of a rinsing solution being accomplished by the same pressure difference as generated between an interior of the second container and the first container for transferring the separation resin.

10. The method according to claim 9, wherein the step of rinsing the at least one first container comprises opening a rinsing valve provided in the connection between the at least one first container and the rinse bag to allow the pressure difference between the first and second containers to transfer rinsing solution from the rinse bag through the at least one first container and finally to the second container and closing the rinse valve when a suitable amount of rinsing solution has been transferred.

11. The method according to claim 1, further comprising the step of:

mixing the separation resin slurry in the second container by using a connected liquid supply system for fluidizing the separation resin slurry inside the second container.

12. The method according to claim 1, wherein the step of transferring separation resin from the at least one first container to the second container by generating a pressure difference between an interior of the second container and an interior of the first container comprises controlling an adaptor provided in the second container.

13. The method according to claim 1, wherein said at least one first container is a flexible bag.

14. The method according to claim 1, wherein said method forms part of a method of packing a column for manufacturing-scale separation of a biopharmaceutical.

* * * * *